United States Patent
Chen et al.

(10) Patent No.: US 9,857,279 B2
(45) Date of Patent: Jan. 2, 2018

(54) SENSOR CHARACTERIZATION APPARATUS, METHODS, AND SYSTEMS

(75) Inventors: Dingding Chen, Tomball, TX (US); Li Gao, Katy, TX (US); Michael T. Pelletier, Houston, TX (US); Nestor Javier Rodriguez, Shenandoah, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 277 days.

(21) Appl. No.: 14/399,377

(22) PCT Filed: Aug. 28, 2012

(86) PCT No.: PCT/US2012/052666
§ 371 (c)(1),
(2), (4) Date: Nov. 6, 2014

(87) PCT Pub. No.: WO2014/035374
PCT Pub. Date: Mar. 6, 2014

(65) Prior Publication Data
US 2015/0101404 A1   Apr. 16, 2015

(51) Int. Cl.
*G01N 9/00* (2006.01)
*E21B 47/10* (2012.01)
*E21B 49/08* (2006.01)

(52) U.S. Cl.
CPC .......... *G01N 9/002* (2013.01); *E21B 47/10* (2013.01); *E21B 49/08* (2013.01)

(58) Field of Classification Search
CPC .......... G01N 9/002; E21B 47/10; E21B 49/08
See application file for complete search history.

(56) References Cited

U.S. PATENT DOCUMENTS

| 3,437,850 A | * | 4/1969 | Bunger | G10H 3/20 |
| | | | | 310/321 |
| 4,170,128 A | * | 10/1979 | Kratky | G01N 9/002 |
| | | | | 73/24.05 |
| 4,491,009 A | * | 1/1985 | Ruesch | G01N 9/002 |
| | | | | 73/32 A |

(Continued)

FOREIGN PATENT DOCUMENTS

| EP | 1109016 A2 | 6/2001 |
| WO | WO-2004011894 A1 | 2/2004 |

(Continued)

OTHER PUBLICATIONS

"European Application Serial No. 12756610.7, Office Action dated Jul. 12, 2016", 3 pgs.

(Continued)

*Primary Examiner* — John Fitzgerald
(74) *Attorney, Agent, or Firm* — Gilliam IP PLLC

(57) ABSTRACT

In some embodiments, an apparatus and a system, as well as a method and an article, may operate to receive a vibration signal having a frequency and a characteristic (e.g., voltage) proportional to the vibration amplitude of a tube in a vibrating tube density sensor. Further activity may include transmitting the density of a fluid flowing through the tube based on the frequency and an elastic modulus of the tube determined by the value of the characteristic. Additional apparatus, systems, and methods are described.

9 Claims, 8 Drawing Sheets

(56) References Cited

U.S. PATENT DOCUMENTS

| | | | | |
|---|---|---|---|---|
| 4,524,610 | A * | 6/1985 | Fitzgerald | G01N 9/002 73/32 A |
| 5,497,665 | A * | 3/1996 | Cage | G01F 1/8409 73/861.356 |
| 5,576,500 | A * | 11/1996 | Cage | G01F 1/8409 73/861.355 |
| 6,378,364 | B1 * | 4/2002 | Pelletier | E21B 47/06 73/152.47 |
| 6,412,354 | B1 * | 7/2002 | Birchak | G01N 9/002 73/861.27 |
| 6,688,176 | B2 * | 2/2004 | Storm, Jr. | G01F 1/8495 73/152.47 |
| 6,912,904 | B2 * | 7/2005 | Storm, Jr. | G01F 1/8495 73/152.47 |
| 9,008,977 | B2 * | 4/2015 | Gao | G01N 35/00 702/1 |
| 2008/0115577 | A1 * | 5/2008 | Headrick | G01N 9/002 73/32 A |
| 2008/0257066 | A1 * | 10/2008 | Henry | G01F 1/8436 73/861.356 |
| 2009/0312977 | A1 * | 12/2009 | Pruysen | G01F 1/8413 702/100 |
| 2011/0167910 | A1 * | 7/2011 | Storm | G01F 1/74 73/32 A |
| 2011/0178738 | A1 * | 7/2011 | Rensing | G01F 1/8413 702/56 |
| 2011/0219872 | A1 * | 9/2011 | Hussain | G01N 9/002 73/32 A |
| 2012/0072128 | A1 | 3/2012 | Gao | |

FOREIGN PATENT DOCUMENTS

| | | |
|---|---|---|
| WO | WO-2006104690 A1 | 10/2006 |
| WO | WO-2014035374 A1 | 3/2014 |

OTHER PUBLICATIONS

"Canadian Application Serial No. 2,882,956, Office Action dated Feb. 1, 2016", 3 pgs.

"Canadian Application Serial No. 2,882,956, Response filed May 5, 2016 to Office Action dated Feb. 1, 2016", 10 pgs.

"European Application Serial No. 12756610.7, Office Action dated Mar. 13, 2015", 2 pgs.

"European Application Serial No. 12756610.7, Reply filed Aug. 27, 2015 to Office Action dated Mar. 13, 2015", 11 pgs.

"International Application Serial No. PCT/US2012/052666, International Preliminary Report on Patentability dated Mar. 12, 2015", 8 pgs.

"International Application Serial No. PCT/US2012/052666, International Search Report dated Jun. 6, 2013", 3 pgs.

"International Application Serial No. PCT/US2012/052666, Written Opinion dated Jun. 6, 2013", 6 pgs.

* cited by examiner

SENSOR CHARACTERIZATION APPARATUS, METHODS, AND SYSTEMS

PRIORITY APPLICATION

This application is a U.S. National Stage Filing under 35 U.S.C. 371 from International Application No. PCT/US2012/052666, filed on 28 Aug. 2012 and published as WO 2014/035374 A1 on 6 Mar. 2014, the application and publication are incorporated herein by reference in their entirety.

BACKGROUND

Understanding the structure and properties of geological formations can reduce the cost of drilling wells for oil and gas exploration. Measurements made in a borehole (i.e., down hole measurements) are typically performed to attain this understanding, to identify the composition and distribution of material that surrounds the measurement device down hole. To obtain such measurements, a variety of sensors are used.

For example, a vibrating tube density sensor can be used down hole to determine formation fluid density. However, the resonance frequency of the vibrating tube within the sensor depends heavily on the elastic modulus of the tube material, which in turn depends upon the tube temperature. Thus, to achieve satisfactory measurement accuracy and resolution under down hole temperature variations, the elastic modulus temperature dependency of the tube material is often established through a comprehensive and time consuming temperature calibration procedure, applied to each sensor before it is used in the field.

DETAILED DESCRIPTION

To address some of the challenges described above, as well as others, apparatus, systems, and methods are described herein that make it easier to use sensors with relatively high temperature sensitivity, such as a vibrating tube density sensors, in down hole applications. Various embodiments of the invention can be used to determine the elastic modulus dependency of the sensor over temperature, so that the effect of temperature on measurement accuracy can be predicted, and reduced. In some embodiments, the value of the elastic modulus during operation can then be determined, without calibration or directly measuring the tube temperature.

To begin, it is noted that a vibrating tube density sensor provides a signal voltage at its output whose amplitude is approximately proportional to the vibration amplitude of the tube. The signal arises from the vibration of a detector magnet inside a detector coil when the tube is driven to vibrate at its resonant frequency. In conventional applications, the voltage signal is used only to indicate the quality of the amplitude of vibration, so that a greater signal amplitude corresponds to greater vibration amplitude.

In various embodiments of the invention, it will be shown that this detector voltage signal can be used in a completely different manner. That is, it can be utilized to determine the elastic modulus of the tube during operation. This type of use can potentially enhance the accuracy of the sensor, perhaps making it possible to dispense with laboratory temperature calibration procedures entirely.

Thus, the purpose of determining the elastic modulus is thus two-fold. In a first aspect, the ability to determine the elastic modulus of the tube in the sensor can improve the overall accuracy of the sensor measurements. In a second aspect, there is an economic impact: determining the elastic modulus of the tube in real time, without calibration, can lead to real savings in both time and money. Various example embodiments that can provide some or all of these advantages will now be described in detail.

Figure 1:
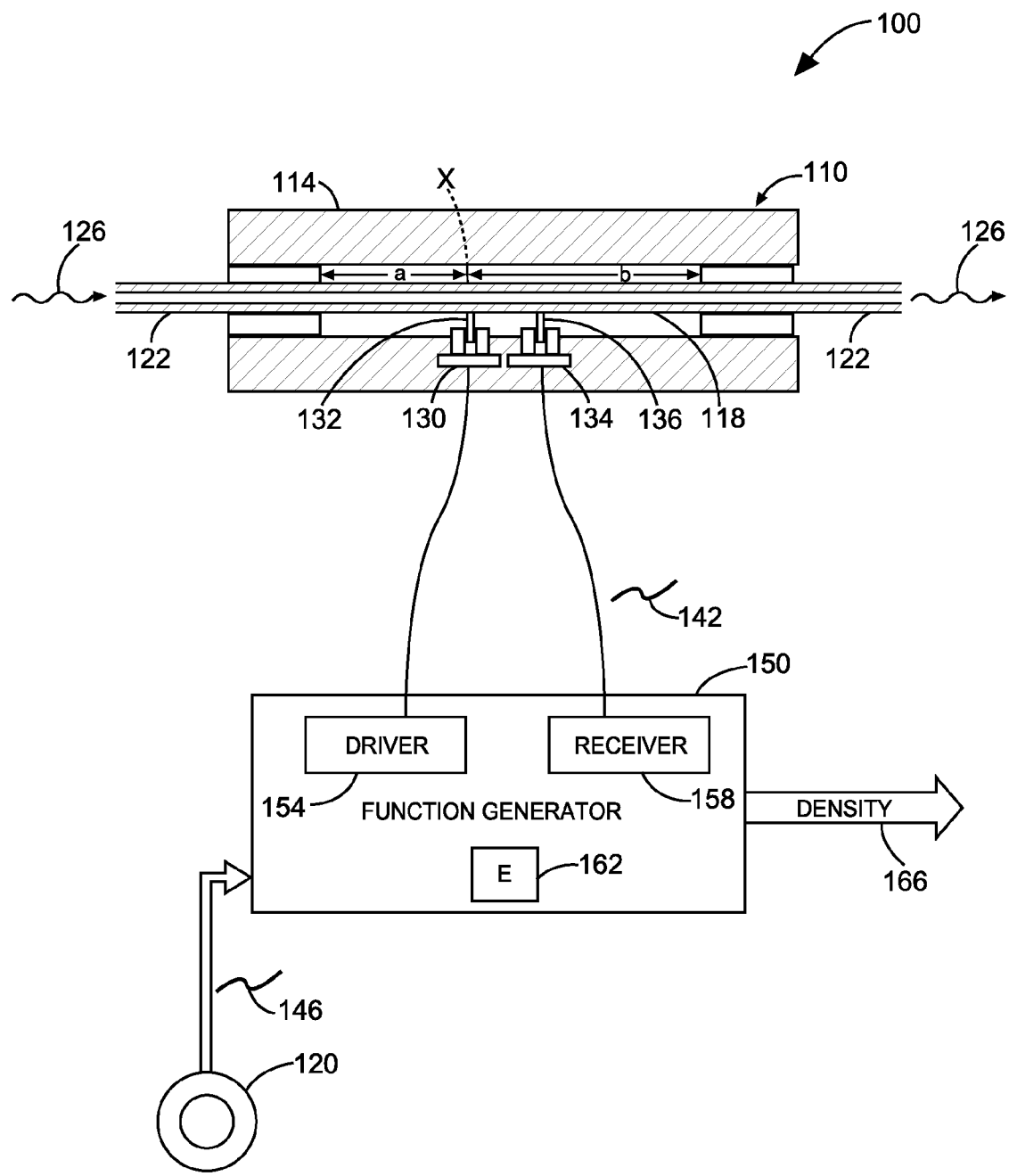
FIG. 1 illustrates a side, cut-away view of a vibrating tube density sensor, forming part of an apparatus configured according to various embodiments of the invention.

FIG. 1 illustrates a side, cut-away view of a vibrating tube density sensor 110, forming part of an apparatus 100 according to various embodiments of the invention. In most embodiments, the density sensor 110 is configured with two sets of coils and magnets: the first set includes a driver coil 130 and a driver magnet 132 (used to set the vibrating tube section 118 in motion), and the second set includes a receiver coil 134 and a receiver magnet 136 (used to monitor the motion of the tube section 118, using a measured characteristic of the signal 142 provided by the receiver coil 134).

To undertake the analysis that leads to determining the elastic modulus in real time, one may consider a logging tool that has a sonde section and an electronics section. When employed down hole, the surrounding formation temperature may cause measurement drift within the electronics section, which in turn produces a change in the response of the sonde. In general, as the environmental temperature increases, the amplitude of the signal (e.g., a voltage) from the receiver coil 134 decreases, up to a point, and thereafter, when the temperature increases even further, the signal output amplitude from the receiver coil 134 also increases.

During operation of the sensor 110, both the frequency and amplitude of the receiver signal 142 are recorded. For example, the measured characteristic of the signal 142 may comprise a voltage or current that is recorded. The frequency can be used to determine the density of the fluid 126 that passes from the flow line 122 into the vibrating tube section 118. The amplitude of the signal 142, while currently only used to indicate vibration quality, can also be used to determine the elastic modulus of the tube, as will now be shown.

One may begin the determination using an expression of the receiver voltage according to Faraday's law, with a partial derivative provided by the chain rule, as shown in equation (1):

$$V = \frac{d\varphi}{dt} = s\frac{dB}{dt} = s\frac{\partial B}{\partial z}\frac{\partial z}{\partial t}, \quad (1)$$

where $\varphi$ is the magnetic flux in the receiver coil 134 Wb, B is the magnetic flux density in the receiver coil 134 in Tesla, and s is the area of the receiver coil 134 in m².

At a distance z away from its surface, the magnetic field along the axis of a permanent disc magnet of radius R and thickness d having a magnetic moment M(T) is given by equation (2):

$$B(T, z) = 4\pi M(T) \cdot \frac{1}{2}\left(\frac{z+d}{\sqrt{R^2 + (z+R)^2}} - \frac{z}{\sqrt{R^2 + z^2}}\right) \quad (2)$$

Since the tube section 118 undergoes harmonic oscillation, the displacement z can be expressed as shown in equation (3):

$$z(T,t) = z_0(T)\sin(\omega t), \quad (3)$$

where $z_0$ is the displacement amplitude of the tube section 118 at the receiver coil 134 position. This amplitude is produced due to the force exerted by the driver coil 130 onto the driver magnet 132. As a function of temperature T, this force can be expressed as shown in equation (4):

$$F(T) = \mu\frac{\partial B}{\partial z} = nsI\frac{\partial B}{\partial z}, \quad (4)$$

where $\mu$ is the magnetic moment of the driver coil 130 in Joules/Tesla (with n-turns that carry current I in an area s). B in this case is the magnetic flux density of the driver magnet 132 in Wb.

Since the vibrating tube section 118 has fixed ends, a point force F(T) imposed at position x, located at distance a from one end and b from the other end (where a+b=L, which is the length of the vibrating portion of the tube section 118), will result in a bending displacement of the tube, which can be obtained by solving the Euler beam equation shown in equation (5):

$$z(x, T) = \frac{F(T)}{6E(T)I}\left[\frac{b^3x^3}{L^3}(L+2a) - \frac{3ab^2x^2}{L^2} - (x-a)^3\right] = G\frac{F(T)}{E(T)}, \quad (5)$$

where E(T) in GPa is the temperature dependent Young's modulus of the tube section 118, I is the area moment of inertia in m⁴. In the right-hand part of equation (5), all geometric parameters have been aggregated into a single geometric factor G.

Combining equations (1)-(5) to produce equation (6), it can be seen that in the end, the receiver coil voltage depends on both the Young's modulus of the tube and the square of the magnetic moment of the magnet, together with a geometric factor g:

$$V(T) = g\frac{[M(T)]^2}{E(T)}. \quad (6)$$

This can be more easily understood when one realizes that both the transmitter and receiver magnets 132, 136 are involved. Assuming each magnet is identical, each contributes one magnetic moment of M(T).

Since the temperature dependence of the magnets is unknown, one can assume a simple polynomial behavior of the magnetic moment over the temperature range, as shown in equation (7):

$$M(T) = M_0 - a_1T - a_2T^2 - a_3T^3 \quad (7)$$

where $a_{1,2,3}$ and $M_0$ are constants.

Thus, equation (6) can be used to determine E(T) once the temperature dependence of the magnetic moment M(T) is known. As will be demonstrated below, even if the magnetic moment M(T) remains unknown, in principle, one can still correlate the receiver coil 134 voltage behavior V=V(T) with the temperature behavior of Young's modulus E=E(T) for the tube section 118.

Since both V(T) and E(T) depend on temperature, substitution to eliminate temperature leads to the expression of Young's modulus as function of receiver voltage E=E(V). In this way, the determination of E(T) may even be achieved in the face of changes that occur via erosion within the tube section 118, due to the abrasive nature of the fluid flowing in the tube.

Therefore, in some embodiments, a function generation device 150 may form part of the apparatus 100. The function generation device 150 may house a driver 154 for the driver coil 130, and a receiver 158 to receive a signal 142 from the receiver coil 134. A temperature sensor 120 may provide a signal 146 that indicates the temperature proximate to the vibrating tube density sensor 110. Using the correlation derived from equations (1)-(6), the Young's modulus E of the tube section 118 can be determined from the value of the temperature indicated by the signals 142, 146. Thereafter, the density 166 of the fluid 126 flowing through the vibrating tube section 118 can also be determined, using the frequency of the signal 142. In some cases, a neural network 162 may form part of the function generation device 150, to supply the value of the Young's modulus E.

Figure 2:
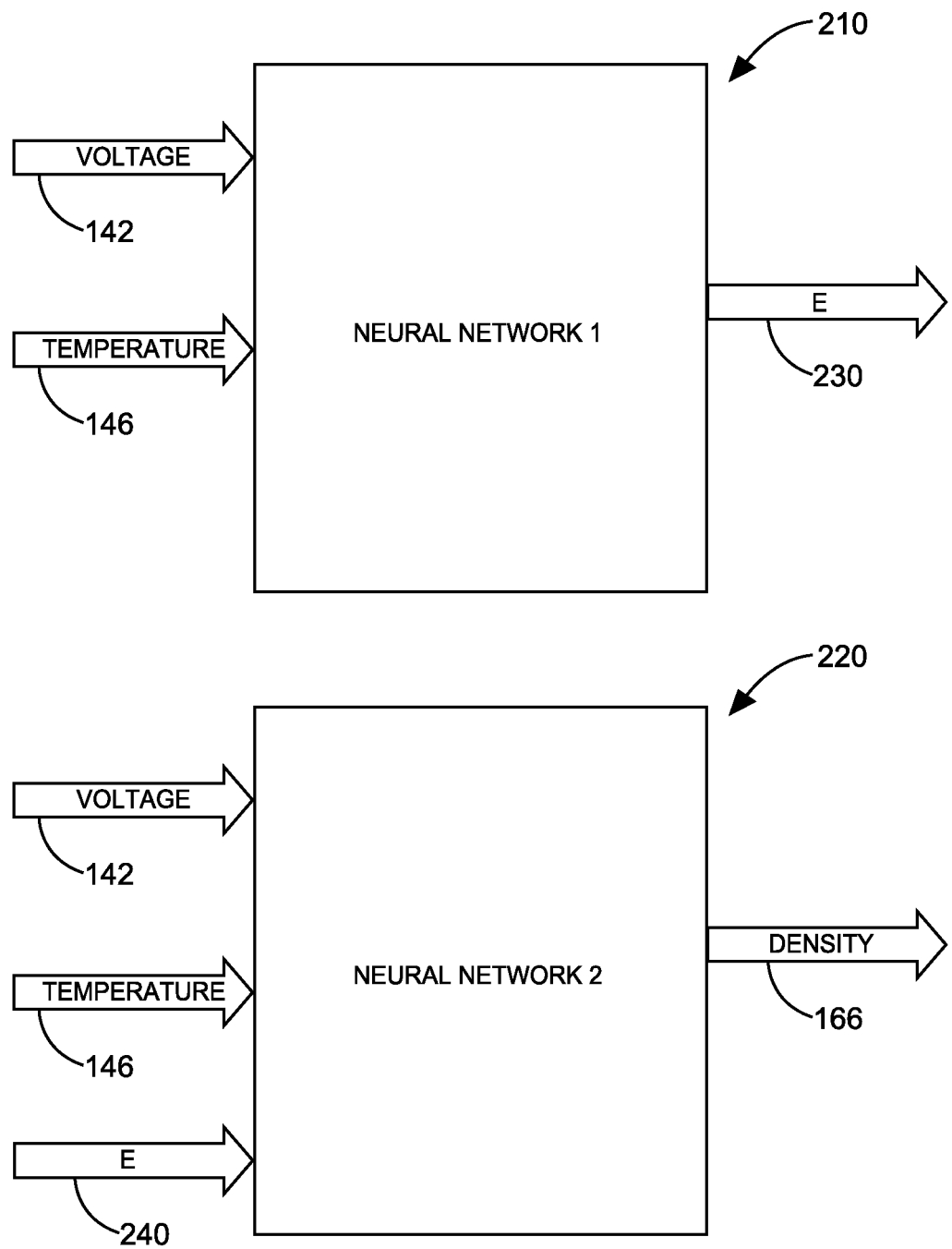
FIG. 2 illustrates two neural network configurations according to various embodiments of the invention.

For example, FIG. 2 illustrates two neural network configurations according to various embodiments of the invention. In each case, a neural network is applied to implement some form of function generation: the Young's modulus 230 for neural network 210 (which is similar to or identical to the neural network 162 of FIG. 1), and the fluid density 166 for neural network 220. This can be achieved by training the network to provide a satisfactory value for the Young's modulus 230, or the density 166, based on the input values of receiver coil signal 142 (e.g., voltage amplitude), temperature 146, and the Young's modulus 240 (e.g., perhaps as provided by measurement, a calibration table, or another neural network). Compared to polynomial curve fitting methods, neural networks sometimes provide better fitting results in a variety of situations.

Figure 3:
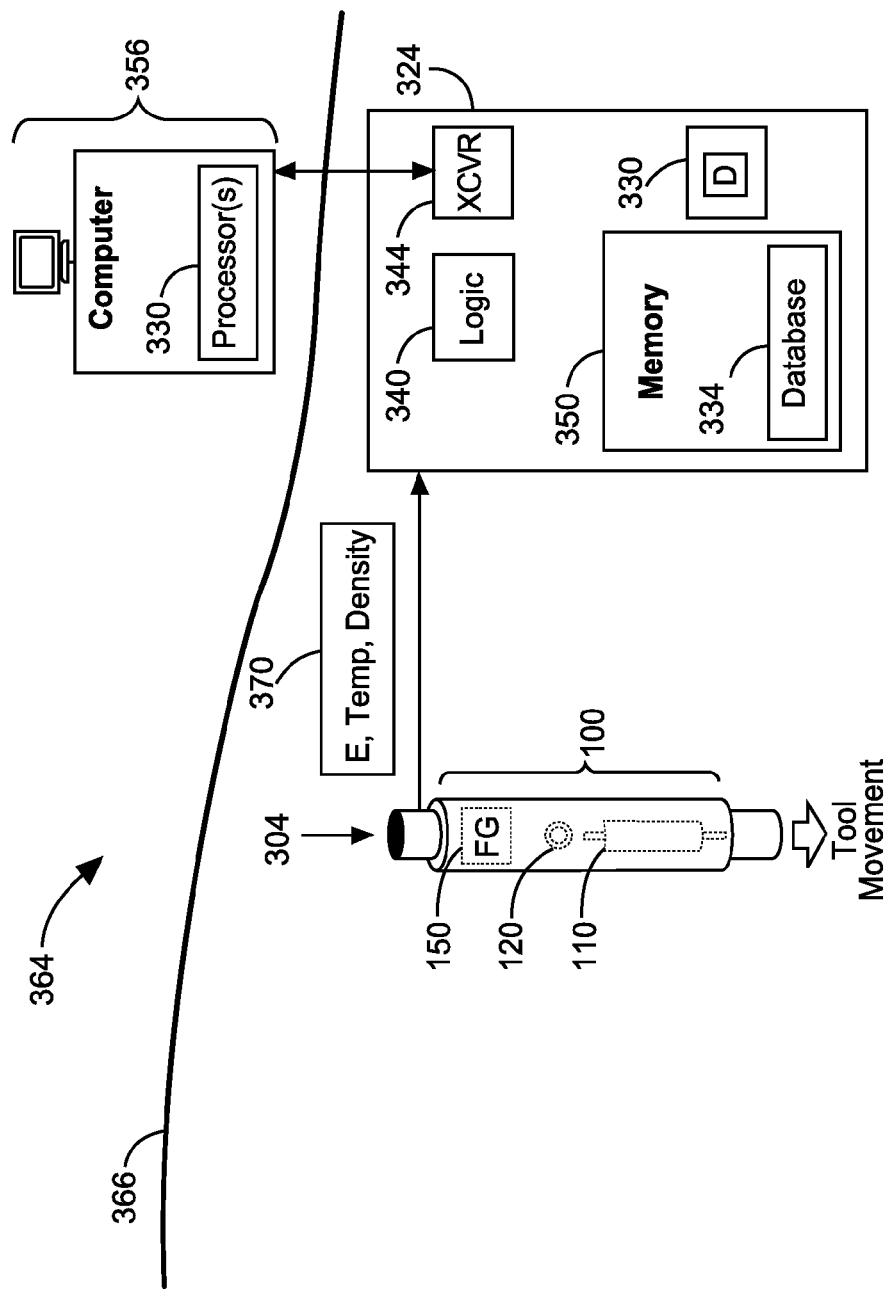
FIG. 3 is a block diagram of apparatus and systems according to various embodiments of the invention

FIG. 3 is a block diagram of apparatus 100 and systems 364 according to various embodiments of the invention. In some embodiments, a system 364 comprises one or more of the apparatus 100, as well as a housing 304. The housing 304 might take the form of a wireline tool body, or a down hole tool. Processor(s) 330 may be located at the surface 366, as part of a surface logging facility 356, or in a data acquisition system 324 above or below the Earth's surface 366, to be packaged with the apparatus 100, including the housing 304. The system 364 may comprise a data transceiver 344 (e.g., a telemetry transmitter and/or receiver) to transmit acquired data 370 from the sensors 110, 120 and the apparatus 100 to the surface logging facility 356. A function generation device 150 may be included in the housing 304 to process sensor signals, as described previously. In addition, or alternatively, logic 340 can be used to acquire and process signals received from the apparatus 100, according to the various methods described herein. Received data can be stored in the memory 350, perhaps as part of a database 334.

Thus, referring now to FIGS. 1-3, it can be seen that many embodiments may be realized. For example, an apparatus 100 may comprise a vibrating tube density sensor 110 and a function generation device 150 to receive a vibration signal having a frequency and a characteristic (e.g., voltage or current) proportional to a vibration amplitude of a tube in the vibrating tube density sensor, and to transmit density of a fluid in the tube based on the frequency and an elastic modulus of the tube determined by the value of the characteristic. Transmission of the fluid density information can occur locally (e.g., transmission to a memory 350 for storage within the same apparatus 100 and/or tool used to house the vibrating tube density sensor 110 and/or the function generation device 150), or remotely (e.g., transmission to a surface logging facility 356, from an apparatus 100 located in a wireline tool that is used to house the vibrating tube density sensor 110 and/or the function generation device 150).

In some embodiments, the function generation device 150 may comprise a number of elements, including a neural network 162, 210, 220, analog and/or digital components. For example, the function generation device 150 may comprise an analog-to-digital converter (e.g., in the receiver 158) to receive the vibration signal 142, and a processor 330 (e.g., in the neural network 162) configured to compute the density 166.

In some embodiments, the environmental temperature may be processed by the function generation device to determine the density. Thus, the function generation device 150 may be configured to receive a temperature signal input, such as signal 146.

In some embodiments, the vibrating tube density sensor may comprise a number of elements, including magnets and coils. Thus, the vibrating tube density sensor may comprise a pair of magnets 132, 136.

In some embodiments, the coils may be divided into transmission and reception functions. Thus, the apparatus 100 may comprise one or more driver coils 130 associated with one of the pair of magnets 132, 136; and one or more receiver coils 134 associated with the other one of the pair of magnets 132, 136.

In some embodiments, the tube in the vibrating tube density sensor may be fixed at both ends, to vibrate in-between the ends. Thus, the tube section 118 may be fixed at each of two ends, to enable vibration at a location along the tube (e.g., at location X) proximate to at least one of the pair of magnets 132, 136. Many other embodiments may be realized, including system embodiments.

For example, a system 364 may comprise a function generation device 150, and a housing 304 attached to a vibrating tube density sensor 110. The function generation device 150 operates as described previously.

The housing may comprise any number of tool types. Thus, in the system 364, the housing may comprise a wireline tool or a measurement while drilling (MWD) tool.

A temperature sensor can be included in the system. Thus, the system may comprise a temperature sensor 120 to provide a temperature signal 146 to the function generation device 150.

The vibrating tube density sensor may be configured to provide the vibration signal as a voltage or current. Thus, the vibrating tube density sensor 110 may generate the vibration signal 142 with the measured/monitored characteristic comprising a voltage provided by a coil 134 disposed within the sensor 110. Additional system embodiments may be realized, and examples of these will now be described.

Figure 4:
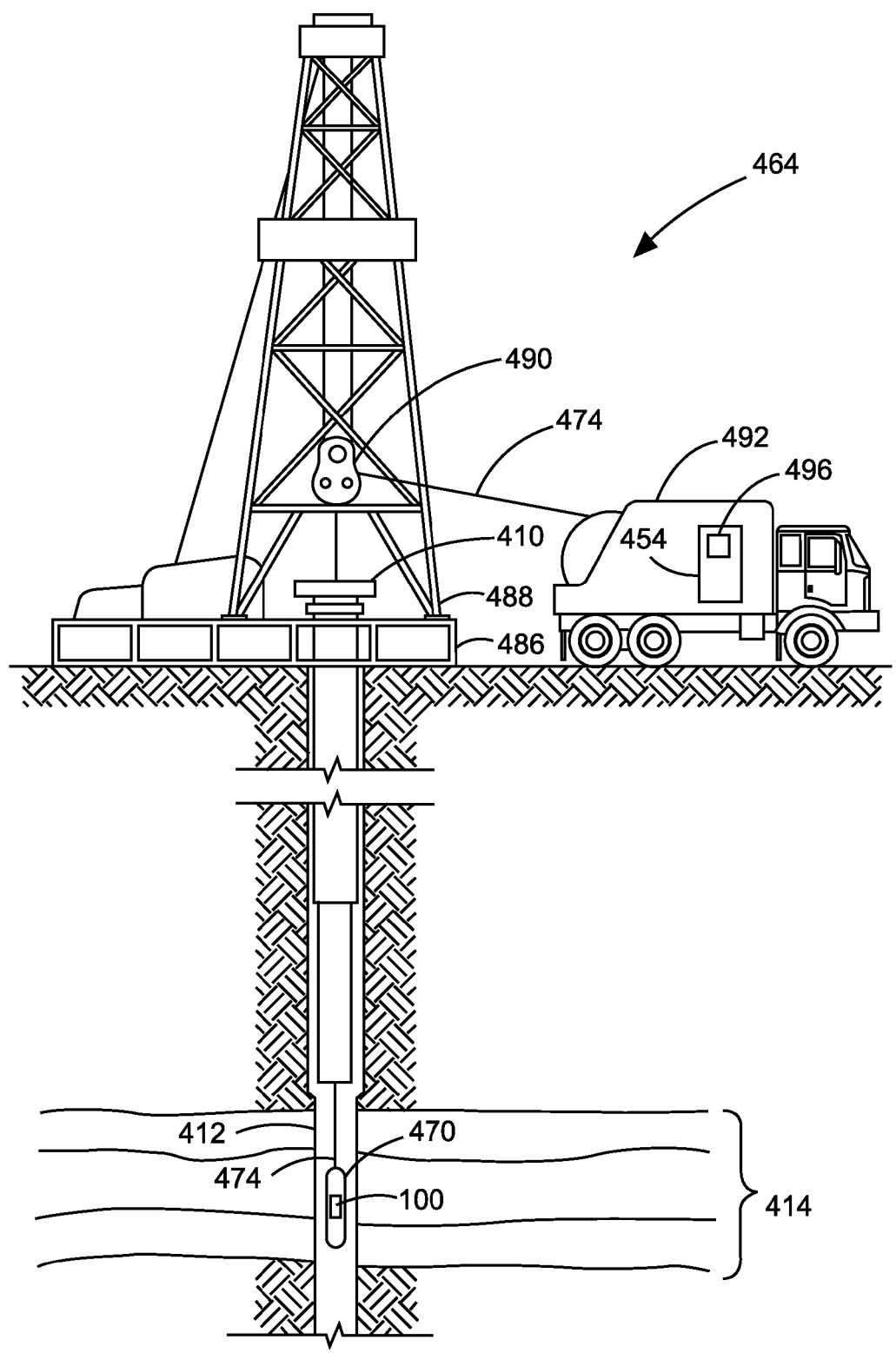
FIG. 4 illustrates a wireline system embodiment of the invention.
Figure 5:
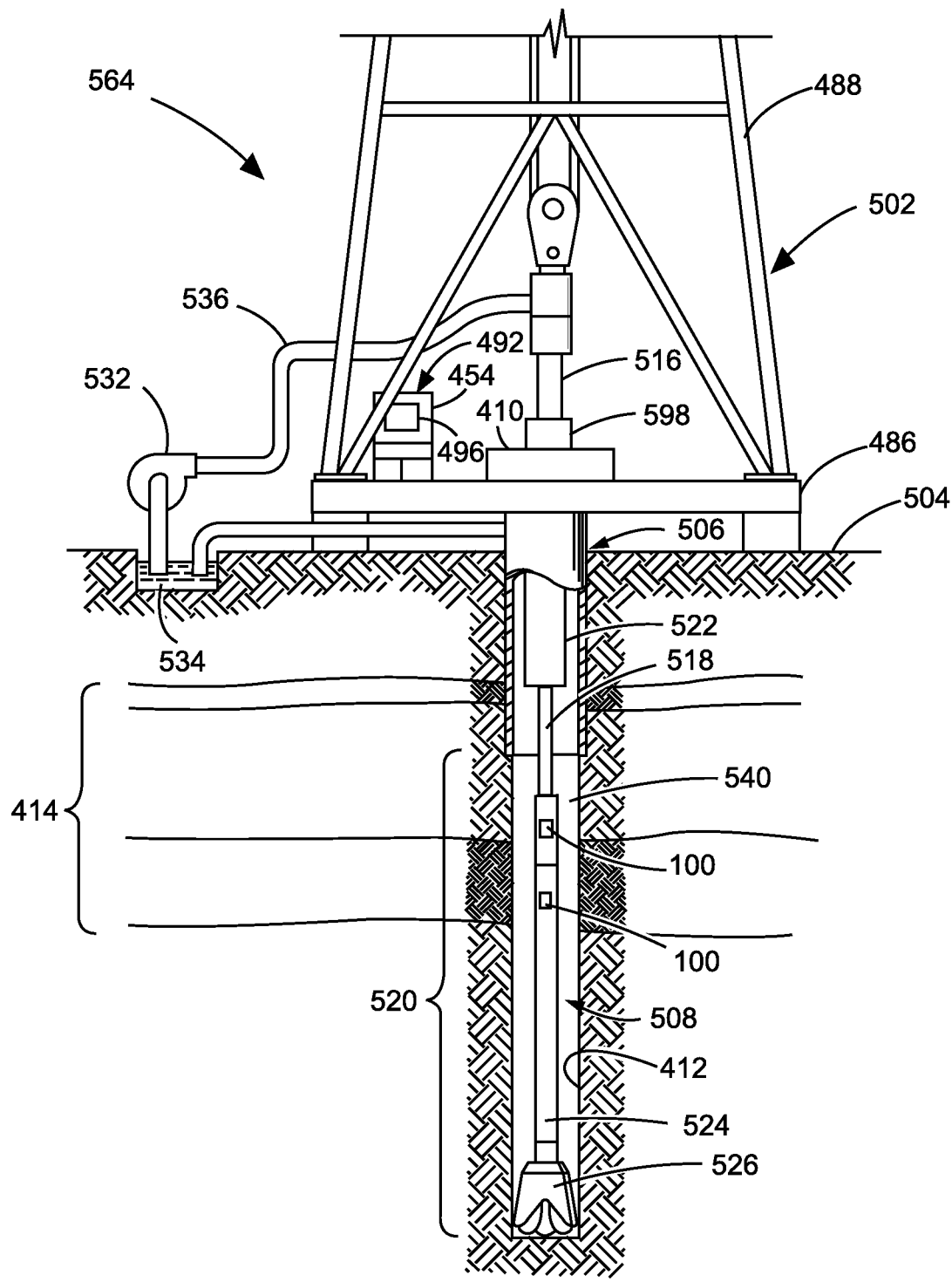
FIG. 5 illustrates a drilling rig system embodiment of the invention.

FIG. 4 illustrates a wireline system 464 embodiment of the invention, and FIG. 5 illustrates a drilling rig system 564 embodiment of the invention. Therefore, the systems 464, 564 may comprise a wireline logging tool body 470 as part of a wireline logging operation, or a down hole tool 524 as part of a down hole drilling operation.

Thus, FIG. 4 shows a well during wireline logging operations. In this case, a drilling platform 486 is equipped with a derrick 488 that supports a hoist 490.

Drilling oil and gas wells is commonly carried out using a string of drill pipes connected together so as to form a drilling string that is lowered through a rotary table 410 into a wellbore or borehole 412. Here it is assumed that the drill string has been temporarily removed from the borehole 412 to allow a wireline logging tool body 470, such as a probe or sonde, to be lowered by wireline or logging cable 474 into the borehole 412. Typically, the wireline logging tool body 470 is lowered to the bottom of the region of interest and subsequently pulled upward at a substantially constant speed.

During the upward trip, at a series of depths various instruments (e.g., portions of the apparatus 100, or system 364 shown in FIGS. 1 and 3) included in the tool body 470 may be used to perform measurements on the subsurface geological formations 414 adjacent the borehole 412 (and the tool body 470). The measurement data can be communicated to a surface logging facility 492 for processing, analysis, and/or storage. The logging facility 492 may be provided with electronic equipment for various types of signal processing, which may be implemented by any one or more of the components of the apparatus 100 or system 364 in FIGS. 1 and 3. Similar formation evaluation data may be gathered and analyzed during drilling operations (e.g., during logging while drilling (LWD) operations, and by extension, sampling while drilling).

In some embodiments, the tool body 470 is suspended in the wellbore by a wireline cable 474 that connects the tool to a surface control unit in the logging facility 492 (e.g., comprising a workstation 454 and display 496). The tool may be deployed in the borehole 412 on coiled tubing, jointed drill pipe, hard wired drill pipe, or any other suitable deployment technique.

Turning now to FIG. 5, it can be seen how a system 564 may also form a portion of a drilling rig 502 located at the surface 504 of a well 506. The drilling rig 502 may provide support for a drill string 508. The drill string 508 may operate to penetrate the rotary table 410 for drilling the borehole 412 through the subsurface formations 414. The drill string 508 may include a Kelly 516, drill pipe 518, and a bottom hole assembly 520, perhaps located at the lower portion of the drill pipe 518.

The bottom hole assembly 520 may include drill collars 522, a down hole tool 524, and a drill bit 526. The drill bit 526 may operate to create the borehole 412 by penetrating the surface 504 and the subsurface formations 414. The down hole tool 524 may comprise any of a number of different types of tools including MWD tools, LWD tools, and others.

During drilling operations, the drill string 508 (perhaps including the Kelly 516, the drill pipe 518, and the bottom hole assembly 520) may be rotated by the rotary table 410. Although not shown, in addition to, or alternatively, the bottom hole assembly 520 may also be rotated by a motor (e.g., a mud motor) that is located down hole. The drill collars 522 may be used to add weight to the drill bit 526. The drill collars 522 may also operate to stiffen the bottom hole assembly 520, allowing the bottom hole assembly 520 to transfer the added weight to the drill bit 526, and in turn, to assist the drill bit 526 in penetrating the surface 504 and subsurface formations 414.

During drilling operations, a mud pump 532 may pump drilling fluid (sometimes known by those of ordinary skill in the art as "drilling mud") from a mud pit 534 through a hose 536 into the drill pipe 518 and down to the drill bit 526. The drilling fluid can flow out from the drill bit 526 and be returned to the surface 504 through an annular area 540 between the drill pipe 518 and the sides of the borehole 412. The drilling fluid may then be returned to the mud pit 534, where such fluid is filtered. In some embodiments, the drilling fluid can be used to cool the drill bit 526, as well as to provide lubrication for the drill bit 526 during drilling operations. Additionally, the drilling fluid may be used to remove subsurface formation cuttings created by operating the drill bit 526.

Thus, referring now to FIGS. 1-5, it may be seen that in some embodiments, systems 464, 564 may include a drill collar 522, a down hole tool 524, and/or a wireline logging tool body 470 to house one or more apparatus 100, similar to or identical to the apparatus 100 described above and illustrated in FIG. 1. Components of the system 364 in FIG. 3 may also be housed by the down hole tool 524 or the tool body 470.

Thus, for the purposes of this document, the term "housing" may include any one or more of a drill collar 522, a down hole tool 524, or a wireline logging tool body 470 (all having an outer surface, to enclose or attach to magnetometers, sensors, fluid sampling devices, density determination devices, pressure measurement devices, temperature measurement devices, transmitters, receivers, acquisition and processing logic, and data acquisition systems). The wireline tool body 470 may comprise a wireline logging tool, including a probe or sonde, for example, coupled to a logging cable 474. The tool 524 may comprise a down hole tool, such as an LWD tool or MWD tool. Many embodiments may thus be realized.

For example, in some embodiments, a system 464, 564 may include a display 496 to present temperature measurement information, as well as Young's modulus information, either measured or processed/calculated, as well as database information, perhaps in graphic form. A system 464, 564 may also include computation logic, perhaps as part of a surface logging facility 492, or a computer workstation 454, to receive signals from transmitters and to send signals to receivers, and other instrumentation to determine properties of the formation 414. Processor(s) 330 may be attached to the housing 304, or located at the surface, as part of a surface computer (e.g., in the surface logging facility 356) as shown in FIG. 3.

The apparatus 100; vibrating tube density sensor 110; vibrating tube section 118; temperature sensor 120; flow line 122; fluid 126; driver coil 130; driver magnet 132; receiver coil 134; receiver magnet 136; signals 142, 146; function generation device 150; driver 154; receiver 158; density 166; neural networks 162, 210, 220; Young's modulus 230; housing 304; processors 330; database 334; logic 340; transceiver 344; memory 350; logging facilities 356, 492; systems 364, 464, 564; data 370; rotary table 410; borehole 412; computer workstations 454; logging tool body 470; logging cable 474; drilling platform 486; derrick 488; hoist 490; display 496; drill string 508; Kelly 516; drill pipe 518; bottom hole assembly 520; drill collars 522; down hole tool 524; drill bit 526; mud pump 532; mud pit 534; and hose 536 may all be characterized as "modules" herein.

Such modules may include hardware circuitry, and/or a processor and/or memory circuits, software program modules and objects, and/or firmware, and combinations thereof, as desired by the architect of the apparatus 100 and systems 364, 464, 564 and as appropriate for particular implementations of various embodiments. For example, in some embodiments, such modules may be included in an apparatus and/or system operation simulation package, such as a software electrical signal simulation package, a power usage and distribution simulation package, a power/heat dissipation simulation package, and/or a combination of software and hardware used to simulate the operation of various potential embodiments.

It should also be understood that the apparatus and systems of various embodiments can be used in applications other than for logging operations, and thus, various embodiments are not to be so limited. The illustrations of apparatus 100 and systems 364, 464, 564 are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, processor modules, embedded processors, data switches, and application-specific modules. Such apparatus and systems may further be included as sub-components within a variety of electronic systems, such as televisions, cellular telephones, personal computers, workstations, radios, video players, vehicles, signal processing for geothermal tools and smart transducer interface node telemetry systems, among others. Some embodiments include a number of methods.

Figure 6:
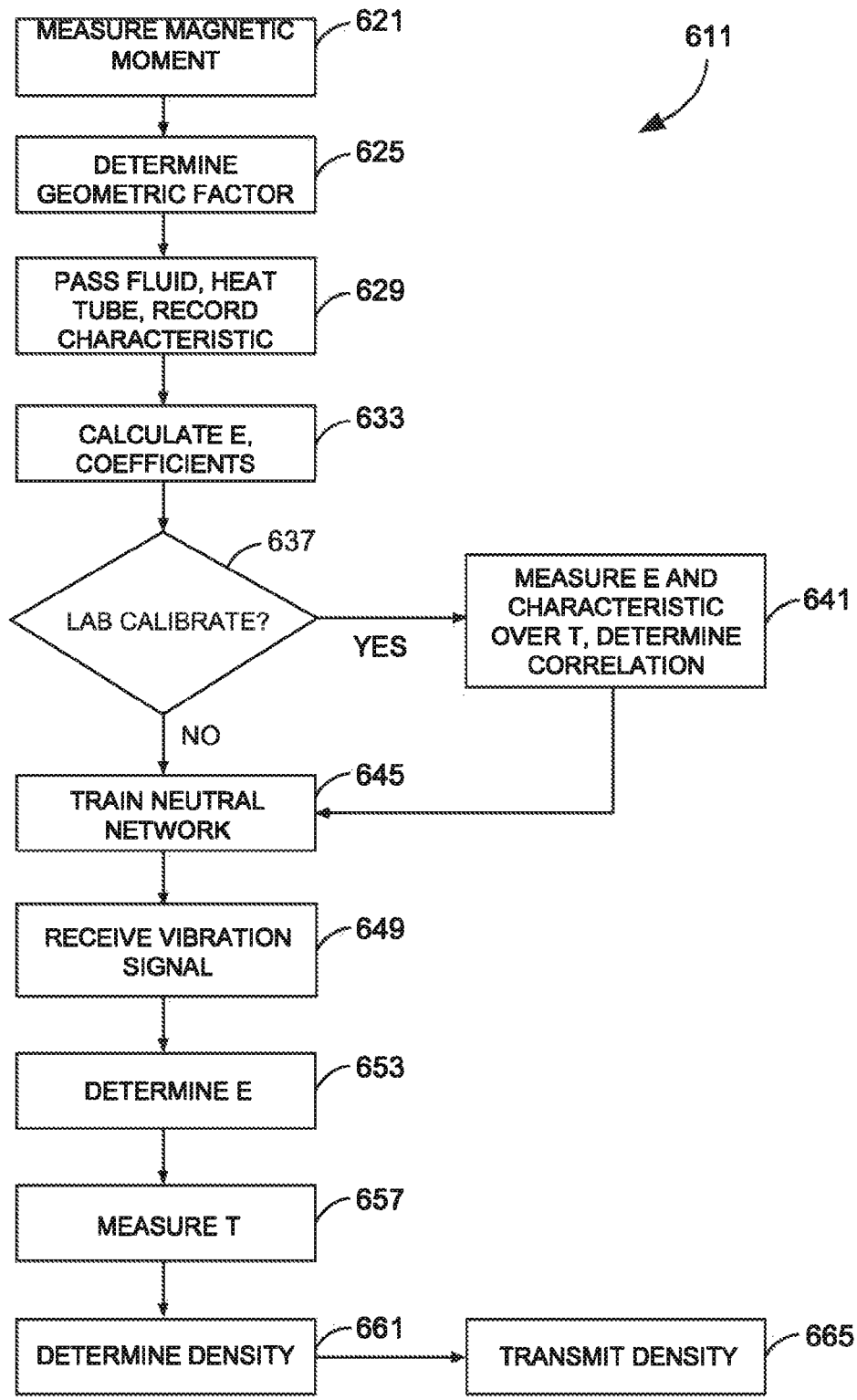
FIG. 6 is a flow chart illustrating several methods according to various embodiments of the invention.

For example, FIG. 6 is a flow diagram illustrating several methods 611 according to various embodiments of the invention. Here it can be seen that a processor-implemented method 611 to determine fluid density using a vibrating tube density sensor, based on a measured environmental temperature, may include, as part of determining the elastic modulus, determining a geometric factor associated with the sensor, based on the measured magnetic moment. Thus, the method 611 may begin at block 621 with measuring the magnetic moment of a receiver magnet in the vibrating tube density sensor over a range of temperatures. The method 611 may continue on to block 625 with determining the geometric factor of the vibrating tube density sensor, based on the magnetic moment. The geometric factor may comprise "G" from equation (5) or "g" from equation (6), depending on the application.

In some embodiments, as part of determining the elastic modulus, the characteristic value (e.g., voltage amplitude of the vibration signal provided by the receiver coil) can be recorded over a range of temperatures, while fluid flows through the tube. Thus, the method 611 may continue on to block 629 with passing a fluid through the tube, heating the tube to a range of known temperatures, and recording the characteristic as a function of the range of known temperatures.

Once the geometric factor, the magnetic moment, and the function defining the characteristic value of temperature are determined (e.g., using values determined as part of the activities in blocks 621, 625, and/or 629), the elastic modulus, and the calibration coefficients associated with the vibrating tube density sensor, can be calculated. Thus, the method 611 may continue on to block 633 to include calculating the elastic modulus, based on the geometric factor, the magnetic moment, and the function; and calculating calibration coefficients based on the elastic modulus.

In some embodiments, a laboratory calibration of the vibrating tube density sensor may be undertaken, to augment the calculations and measurements of sensor characteristics. If this type of calibration is not desired, the method 611 may continue on to block 645. Otherwise, to find a correlation between the elastic modulus and the characteristic to be measured, so that density can be determined directly from the characteristic when the temperature is known, the method 611 may include, at block 641, measuring the elastic modulus and the sensor signal characteristic over a range of temperatures, and determining a correlation between the elastic modulus and the characteristic as a function that is used to provide the value of the elastic modulus based on the value of the characteristic.

The method 611 may include, at block 645, training a neural network to provide the elastic modulus of the tube based on the measured signal characteristic and the temperature, or perhaps the density directly from a measured signal characteristic, the temperature, and a measured or tabulated value of the elastic modulus.

The method 611 may continue on to block 649 to include receiving a vibration signal having a frequency and a characteristic proportional to the vibration amplitude of the tube in the vibrating tube density sensor.

In some embodiments, the characteristic value may depend on a quality factor, or a receiver coil voltage, associated with vibration by the tube. Thus, the characteristic may comprise a quality factor of the vibrating tube density sensor, or a voltage provided by a receiver coil disposed within the sensor.

In some embodiments, the elastic modulus of the tube may be determined, at least in part, by the magnetic moment and the measured value of the signal characteristic. Thus, the method 611 may include, at block 653, determining the elastic modulus by the value of the characteristic and the magnetic moment of at least one receiver magnet disposed within the sensor.

In some embodiments, a generation function model can be developed for implementation in an analog or digital function generation device, to determine the elastic modulus of the sensor. Thus, the activity at block 653 may comprise processing the value of the characteristic using a generation function model based on a polynomial function or a trained neural network to obtain the elastic modulus.

In some embodiments, the elastic modulus of the sensor tube can be measured over temperature, and the resulting behavior can be used to train a neural network (e.g., to provide fluid density as a direct output of the network). Thus, the activity at block 653 may comprise determining the elastic modulus by providing the vibrating tube density sensor signal to a voltage-to-elastic modulus function model forming part of a trained neural network, the network being previously trained over a range of measured temperature behavior associated with the vibrating tube density sensor.

Once a behavior model is developed for the vibrating tube density sensor, perhaps embodied by an analog computer or a neural network, temperature near the tube can be measured, and used to determine the density of the fluid in the tube based on the measured characteristic value. Thus, the method 611 may include, at block 657, determining a temperature proximate to the tube. The method 611 may continue on to block 661 to include determining the fluid density based on the temperature.

The method 611 may continue on to block 665 to include transmitting the density of the fluid flowing through the tube based on the frequency and an elastic modulus of the tube, as determined by the value of the characteristic.

As an aid to understanding how various embodiments might be implemented in practice, more specific examples of the method 611 will now be described, without relating each activity to any particular part of the flow diagram in FIG. 6.

In a first example, temperature calibration can be used to augment the determination of fluid density using measured vibration signal characteristics. In this case, the relationship between the magnetic moment M(T) and temperature of the magnets can be experimentally determined by measuring the magnetic moment M(T) as function of temperature using a Vibrating Sample Magnetometer (VSM), or a Superconducting Quantum Interference Device (SQUID), among others. The geometric factor g in equation (6) can also be experimentally determined by measuring both E and V at a fixed temperature. With a known standard fluid such as water in the sensor, the sensor can be heated to different temperatures while continuously exciting the sensor into resonance using the driver coil. The receiver voltage amplitude is then recorded as function of temperature V(T). At this point, equation (6) can be used to derive the elastic modulus E(T). From the elastic modulus E(T), the calibration coefficients for E(T) can be derived and stored for real time recall.

In some embodiments, if E(T) is already established (for example, it has been obtained using a conventional calibration procedure), a one-to-one correlation between E(T) and V(T) (see FIG. 9) can be established. In this case, a measured receiver signal characteristic (e.g., a voltage magnitude) will yield a corresponding elastic modulus E(T) at given temperature during operation. This is so because E(T) is known, via the previously-determined correspondence between E(T) and V(T).

In a second example, no temperature calibration is used. To begin, the relationship between the magnetic moment M(T) and temperature of the magnets can again be experimentally determined by measuring the magnetic moment M(T) as function of temperature. The geometric factor g in equation (6) is again experimentally determined by measuring both E and V at a fixed temperature.

At this point, while the vibrating tube density sensor is being used in the field, the receiver coil characteristic is measured (e.g., voltage amplitude), and equation (6) is used to determine the elastic modulus E. This value is used directly in a conventional density determination algorithm, to determine the density of the fluid flowing through the vibrating tube density sensor.

It should be noted that the methods described herein do not have to be executed in the order described, or in any particular order. Moreover, various activities described with respect to the methods identified herein can be executed in iterative, serial, or parallel fashion. The various elements of each method can be substituted, one for another, within and between methods. Information, including parameters, commands, operands, and other data, can be sent and received in the form of one or more carrier waves.

Upon reading and comprehending the content of this disclosure, one of ordinary skill in the art will understand the manner in which a software program can be launched from a computer-readable medium in a computer-based system to execute the functions defined in the software program. One of ordinary skill in the art will further understand the various programming languages that may be employed to create one or more software programs designed to implement and perform the methods disclosed herein. For example, the programs may be structured in an object-orientated format using an object-oriented language such as Java or C#. In another example, the programs can be structured in a procedure-orientated format using a procedural language, such as assembly or C. The software components may communicate using any of a number of mechanisms well known to those skilled in the art, such as application program interfaces or interprocess communication techniques, including remote procedure calls. The teachings of various embodiments are not limited to any particular programming language or environment. Thus, other embodiments may be realized.

Figure 7:
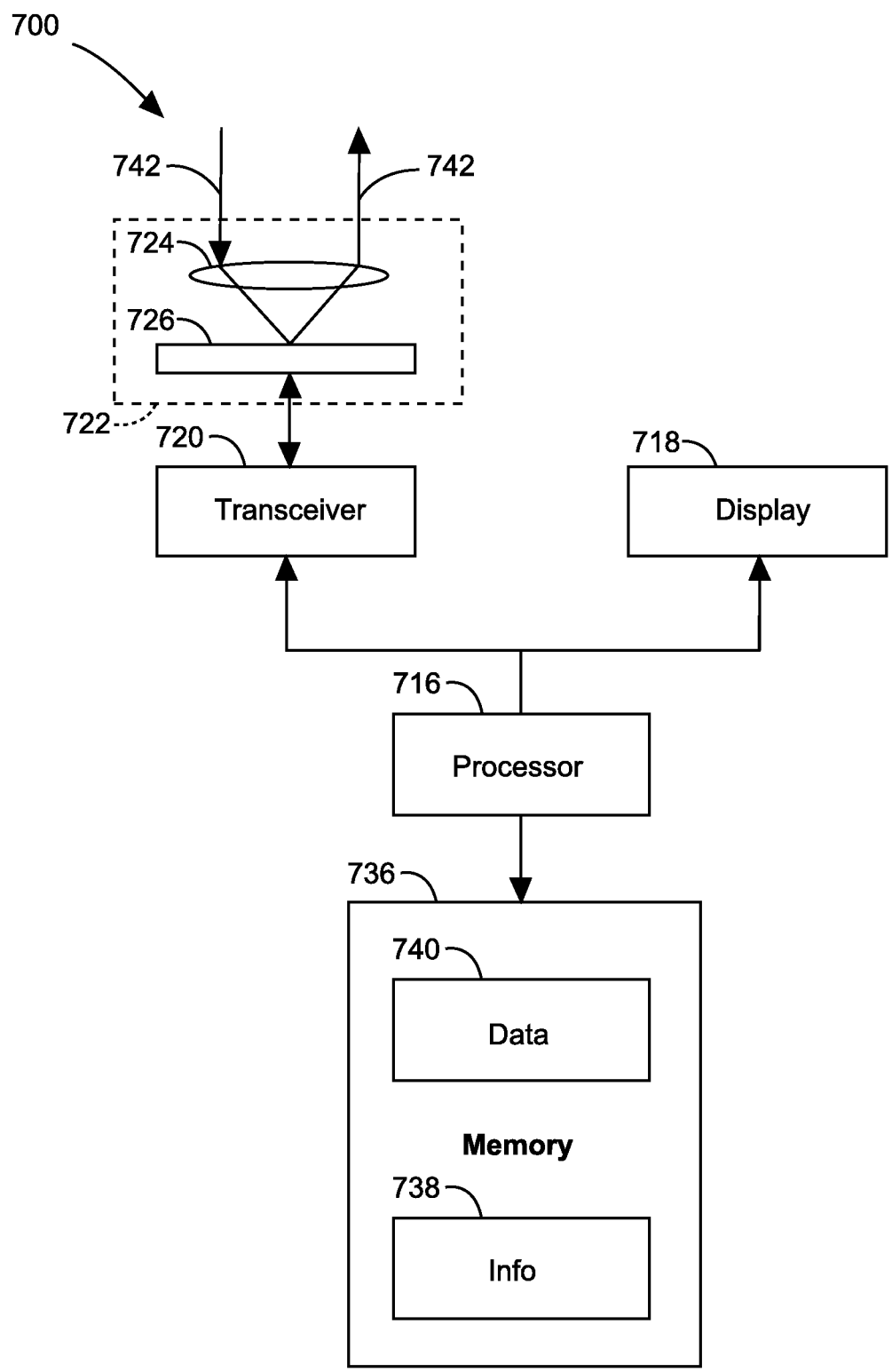
FIG. 7 is a block diagram of an article according to various embodiments of the invention.

For example, FIG. 7 is a block diagram of an article 700 of manufacture according to various embodiments, such as a computer, a memory system, a magnetic or optical disk, or some other storage device. The article 700 may include one or more processors 716 coupled to a machine-accessible medium such as a memory 736 (e.g., removable storage media, as well as any tangible, non-transitory memory including an electrical, optical, or electromagnetic conductor) having associated information 738 (e.g., computer program instructions and/or data), which when executed by one or more of the processors 716, results in a machine (e.g., the article 700) performing any actions described with respect to the apparatus of FIG. 1, the systems of FIGS. 3, 4, and 5; and the methods of FIG. 6. The processors 716 may comprise one or more processors sold by Intel Corporation (e.g., Intel® Core™ processor family), Advanced Micro Devices (e.g., AMD Athlon™ processors), and other semiconductor manufacturers.

In some embodiments, the article 700 may comprise one or more processors 716 coupled to a display 718 to display data processed by the processor 716 and/or a wireless transceiver 720 (e.g., a down hole telemetry transceiver) to receive and transmit data processed by the processor.

The memory system(s) included in the article 700 may include memory 736 comprising volatile memory (e.g., dynamic random access memory) and/or non-volatile memory. The memory 736 may be used to store data 740 processed by the processor 716.

In various embodiments, the article 700 may comprise a communication apparatus 722, which may in turn include amplifiers 726 (e.g., preamplifiers or power amplifiers) and one or more antennas 724 (e.g., transmitting antennas and/or receiving antennas). Signals 742 received or transmitted by the communication apparatus 722 may be processed according to the methods described herein.

Many variations of the article 700 are possible. For example, in various embodiments, the article 700 may comprise a down hole tool, including the apparatus 100 shown in FIG. 1. In some embodiments, the article 700 is similar to or identical to the apparatus 100 or system 346 shown in FIGS. 1 and 3.

For those readers that desire additional information regarding the development of the mechanisms described herein, the details of relationships between various measurements and corresponding values indicated by a vibrating tube density sensor will now be discussed.

Figure 8:
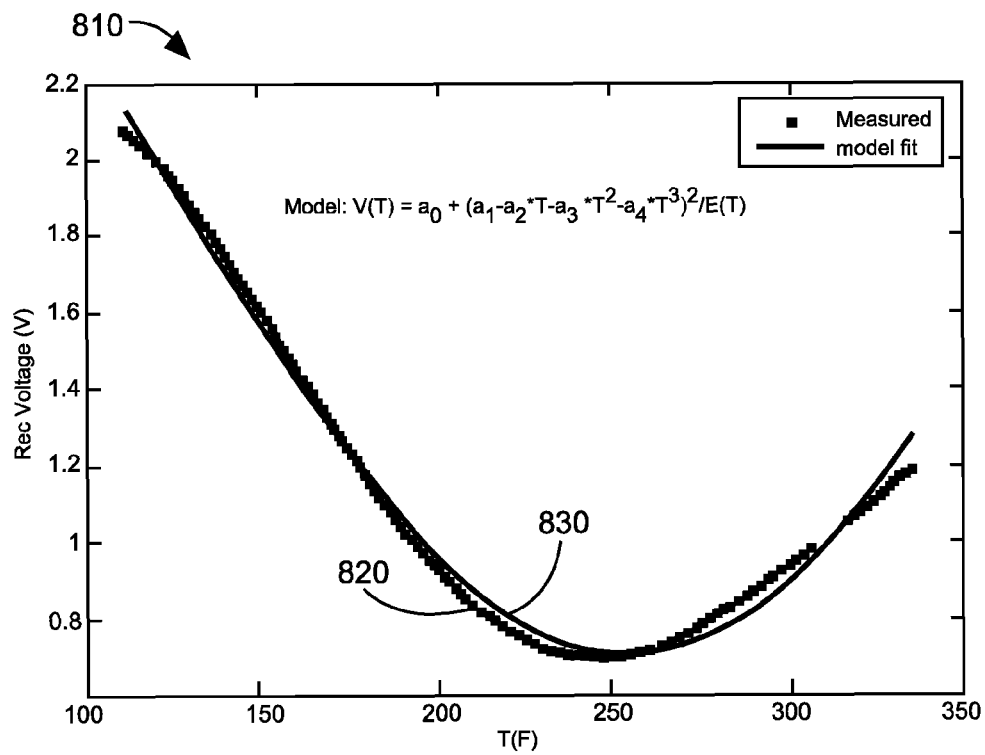
FIG. 8 provides a comparison between the measured output from a vibrating tube density sensor, and modeled output from the sensor, over temperature, according to various embodiments of the invention.

To begin, FIG. 8 provides a comparison between the measured output 820 from a vibrating tube density sensor, and modeled output 830 from the sensor, over temperature, according to various embodiments of the invention. Here, equation (7) is used to fit the polynomial model to the measured receiver voltage.

The graph 810 serves to show that even if $M(T)$ remains unknown, one can still find a good correlation between the receiver coil voltage behavior $V=V(T)$, and a model of the receiver coil voltage, by assuming that $M(T)$ has a polynomial temperature dependence when the Young's modulus $E(T)$ of the tube in the sensor is known (e.g., via measurement in a laboratory). With a more complex model for magnet behavior, the fit to temperature data should further improve.

Figure 9:
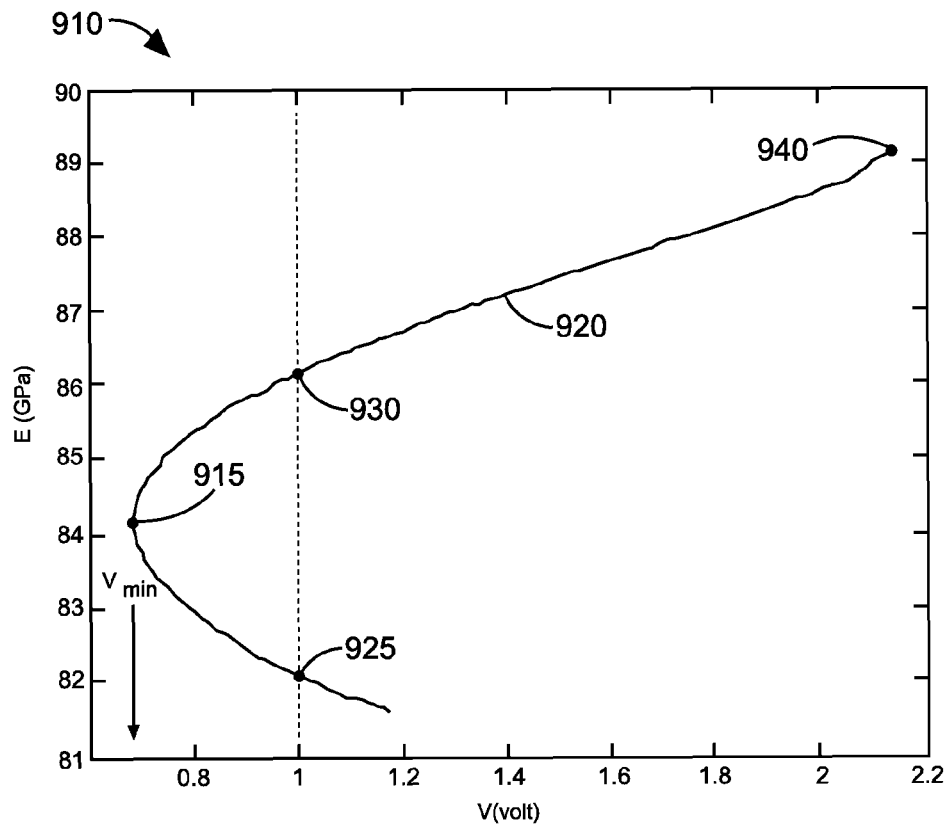
FIG. 9 illustrates a measured relationship between the elastic modulus of a vibrating tube and the receiver coil voltage in a vibrating tube density sensor, according to various embodiments of the invention.

To continue, FIG. 9 illustrates a measured relationship between the elastic modulus of a vibrating tube and the receiver coil voltage in a vibrating tube density sensor, according to various embodiments of the invention.

As noted previously, during the development of equations (1)-(7), eliminating temperature via substitution leads to the expression of Young's modulus as function of receiver voltage $E=E(V)$. This is demonstrated in the graph 910. The double-valued function can be made into a single-valued one by noting the particular temperature at which the receiver voltage is a minimum (in the graph 910, this point 915 occurs at a receiver voltage of about 0.65 volts). Thus, if one has a known value of the measured voltage, such as 1.0 volt, a vertical line drawn across the curve 920 at this point will intercept the curve 920 at two places 925, 930. Since there is only one value for Young's modulus E at a given temperature, the correct value of the modulus (about 86 GPa, in this case) can be determined by noting where the minimum voltage value point 915 occurs on the curve 920, to resolve the double-value problem by picking the correct place 930 on the curve as the point corresponding to the measured voltage of 1.0 volt along the portion of the curve 920 that provides a continuum of increasing modulus values, from the minimum voltage point 915, to the maximum voltage point 940.

In summary, the apparatus, systems, and methods disclosed herein may serve to reduce or even eliminate the use of time-consuming laboratory calibration procedures. Moreover, the receiver coil voltage, formerly used only to provide an indication of signal quality from the sensor, can now be used directly to provide the elastic modulus of the tube over temperature, reducing the uncertainty in the final density determination, especially under low or no flow conditions. To further reduce error, in some embodiments, the method of determining $E(T)$ disclosed herein and the existing method of heated calibration in a laboratory, prior to field use, can be combined. This augmented process provides additional data points, to make interpolation easier between measured values. Reduced data acquisition cost, greater sensor accuracy, and increased client satisfaction may result.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A method, comprising:
   passing a fluid through a vibrating tube section of a vibrating tube density sensor;
   heating the vibrating tube section over a range of temperatures;
   measuring a magnetic moment of a receiver magnet in the vibrating tube density sensor over the range of temperatures;
   determining a geometric factor of the vibrating tube density sensor, based on the measured magnetic moment;
   receiving a vibration signal having a frequency and a characteristic proportional to a vibration amplitude of the vibrating tube section;
   determining an elastic modulus based, at least in part, on the geometric factor, the magnetic moment, and a temperature dependent function of the characteristic; and
   determining density of a fluid flowing through the vibrating tube section based on the frequency and the elastic modulus.

2. The method of claim 1, wherein the characteristic comprises a quality factor of the vibrating tube density sensor or a voltage provided by a receiver coil disposed within the vibrating tube density sensor.

3. The method of claim 1, further comprising:
   processing the value of the characteristic using a generation function model based on a polynomial function or a trained neural network to obtain the elastic modulus.

4. The method of claim 1, further comprising:
   determining the elastic modulus by providing the vibration signal to a voltage-to-elastic modulus function model forming part of a trained neural network, the trained neural network being previously trained over a range of measured temperature behavior associated with the vibrating tube density sensor.

5. The method of claim 1, further comprising:
   measuring an elastic modulus and the characteristic over a range of temperatures; and
   determining a correlation between the measured elastic modulus and the characteristic value as a function that is used to provide a value of the elastic modulus based on the value of the characteristic.

6. The method of claim 1, further comprising:
   recording the characteristic as a function of the range of temperatures.

7. The method of claim 6, further comprising:
   calculating the elastic modulus, based on the geometric factor, the magnetic moment, and the function; and
   calculating calibration coefficients based on the elastic modulus.

8. The method of claim 1, further comprising:
   determining a temperature proximate to the vibrating tube section; and
   determining the density based on the temperature.

9. The method of claim 8, wherein determining the temperature proximate to the tube comprises using an emissive sensor.

* * * * *